US012741069B2

(12) United States Patent
Fujiwara et al.

(10) Patent No.: US 12,741,069 B2
(45) Date of Patent: Sep. 22, 2026

(54) BLOOD PURIFICATION DEVICE HAVING IMPROVED SERVICEABILITY

(71) Applicant: NIKKISO CO., LTD., Tokyo (JP)

(72) Inventors: Masato Fujiwara, Makinohara (JP); Yuya Menjoh, Makinohara (JP); Makoto Ishida, Makinohara (JP); Tomohiko Yabe, Makinohara (JP)

(73) Assignee: NIKKISO CO., LTD, Tokyo (JP)

( * ) Notice: Subject to any disclaimer, the term of this patent is extended or adjusted under 35 U.S.C. 154(b) by 266 days.

(21) Appl. No.: 18/565,987

(22) PCT Filed: May 26, 2022

(86) PCT No.: PCT/JP2022/021612

§ 371 (c)(1), (2) Date: Nov. 30, 2023

(87) PCT Pub. No.: WO2022/255225

PCT Pub. Date: Dec. 8, 2022

(65) Prior Publication Data

US 2024/0252728 A1 Aug. 1, 2024

(30) Foreign Application Priority Data

Jun. 2, 2021 (JP) ................................ 2021-093303

(51) Int. Cl.
*A61M 1/16* (2006.01)

(52) U.S. Cl.
CPC ........ *A61M 1/1656* (2013.01); *A61M 1/1607* (2014.02); *A61M 2205/10* (2013.01);
(Continued)

(58) Field of Classification Search
CPC .............. A61M 1/1656; A61M 1/1607; A61M 2205/10; A61M 2205/126;
(Continued)

(56) References Cited

U.S. PATENT DOCUMENTS 5,895,571 A 4/1999 Utterberg
10,682,451 B2 6/2020 Masuda et al.
(Continued)

FOREIGN PATENT DOCUMENTS

CA 2157169 A1 3/1996
JP 2010-184029 A 8/2010
(Continued)

OTHER PUBLICATIONS

First Office Action from the China National Intellectual Property Administration (CNIPA) issued on Dec. 22, 2025, 11 pages; English translation 10 pages.

(Continued)

*Primary Examiner* — Hayden Brewster
(74) *Attorney, Agent, or Firm* — Calderon Safran & Wright P.C.

(57) ABSTRACT

A blood purification device to perform blood purification treatment through a blood purifier, the blood purification device includes a dialysate supply-and-discharge unit that supplies a dialysate to the blood purifier and discharges a waste liquid from the blood purifier, an extracorporeal circulation unit including an extracorporeal circulation part to extracorporeally circulate blood of a patient through the blood purifier, and a control unit capable of controlling the dialysate supply-and-discharge unit and the extracorporeal circulation unit. The dialysate supply-and-discharge unit includes a water removal control part to control an amount of water removed from the blood. The extracorporeal circulation unit is configured as a separate component from the dialysate supply-and-discharge unit.

12 Claims, 3 Drawing Sheets

(52) U.S. Cl.
CPC ... *A61M 2205/126* (2013.01); *A61M 2205/18* (2013.01); *A61M 2205/3303* (2013.01); *A61M 2205/3327* (2013.01); *A61M 2205/3331* (2013.01); *A61M 2205/3569* (2013.01); *A61M 2205/3592* (2013.01); *A61M 2205/502* (2013.01); *A61M 2209/082* (2013.01); *A61M 2209/084* (2013.01); *A61M 2230/30* (2013.01)

(58) Field of Classification Search
CPC ...... A61M 2205/18; A61M 2205/3303; A61M 2205/3327; A61M 2205/3331; A61M 2205/3569; A61M 2205/3592; A61M 2205/502; A61M 2209/082; A61M 2209/084; A61M 2230/30; A61M 1/3626; A61M 2205/3306; A61M 2205/3344; A61M 1/3413
USPC .......................................................... 210/647
See application file for complete search history.

(56) References Cited

U.S. PATENT DOCUMENTS

| | | | |
|---|---|---|---|
| 2003/0010719 | A1 | 1/2003 | Brugger et al. |
| 2009/0008306 | A1 | 1/2009 | Cicchello et al. |
| 2011/0189048 | A1 | 8/2011 | Curtis et al. |
| 2018/0133385 | A1 | 5/2018 | Masuda et al. |
| 2021/0060228 | A1 | 3/2021 | Matsuo et al. |
| 2022/0088280 | A1 | 3/2022 | Furuhashi et al. |

FOREIGN PATENT DOCUMENTS

| | | | |
|---|---|---|---|
| JP | 2019-126530 | A | 8/2019 |
| JP | 2020-103834 | A | 7/2020 |
| WO | 2016/171023 | A1 | 10/2016 |

OTHER PUBLICATIONS

Extended European Search Report, Application No. 22815975.2-1113 / 4331637 PCT/JP2022021612, dated Mar. 31, 2025, 8 pages.

Japanese Office Action of counterpart Japanese patent application JP 2023-525775, dated Jun. 2, 2026, English and Japanese copy attached.

China National Intellectual Property Administration (CNIPA) issued Second Office Action dated Jun. 6, 2026 on counterpart CN Application No. 202280039760.6, English and Chinese copy attached.

China National Intellectual Property Administration (CNIPA) issued Second Office Action dated Aug. 7, 2026 on counterpart CN Application No. 202280039760.6, English and Chinese copy attached. (18 Pages).

BLOOD PURIFICATION DEVICE HAVING IMPROVED SERVICEABILITY

TECHNICAL FIELD

The present invention relates to a blood purification device to perform blood purification treatment through a blood purifier.

BACKGROUND OF THE INVENTION

An integrated-type blood purification device, which integrally includes a dialysate supply-and-discharge portion to supply and discharge dialysate to and from a blood purifier and an extracorporeal circulation portion to extracorporeally circulate blood of a patient through the blood purifier, is known as a conventional blood purification device to perform blood purification treatment through a blood purifier (see, e.g., Patent Literature 1).

Patent Document 2 can be found as prior art document information related to the invention of the present application.

CITATION LIST

Patent Literatures

Patent Literature 1: JP 2020-103834A

Patent Literature 2: US Patent Application Publication No. 2003/0010719, Specification

SUMMARY OF THE INVENTION

With conventional integrated-type blood purification devices, workers generally travel to installation locations of blood purification devices to perform maintenance work. In recent years, the number of home blood purification treatments is increasing and there is a need for blood purification devices with further improved maintainability.

Therefore, it is an object of the invention to provide a blood purification device with improved maintainability.

A blood purification device in an embodiment of the invention is a blood purification device to perform blood purification treatment through a blood purifier, and comprises:

- a dialysate supply-and-discharge unit that supplies a dialysate to the blood purifier and discharges a waste liquid from the blood purifier;
- an extracorporeal circulation unit comprising an extracorporeal circulation part to extracorporeally circulate blood of a patient through the blood purifier; and
- a control unit capable of controlling the dialysate supply-and-discharge unit and the extracorporeal circulation unit,
- wherein the dialysate supply-and-discharge unit comprises a water removal control part to control an amount of water removed from the blood, and
- wherein the extracorporeal circulation unit is configured as a separate component from the dialysate supply-and-discharge unit.

Advantageous Effects of the Invention

According to the invention, it is possible to provide a blood purification device with improved maintainability.

DETAILED DESCRIPTION OF THE INVENTION

Embodiment

An embodiment of the invention will be described below in conjunction with the appended drawings.

Figure 1A:
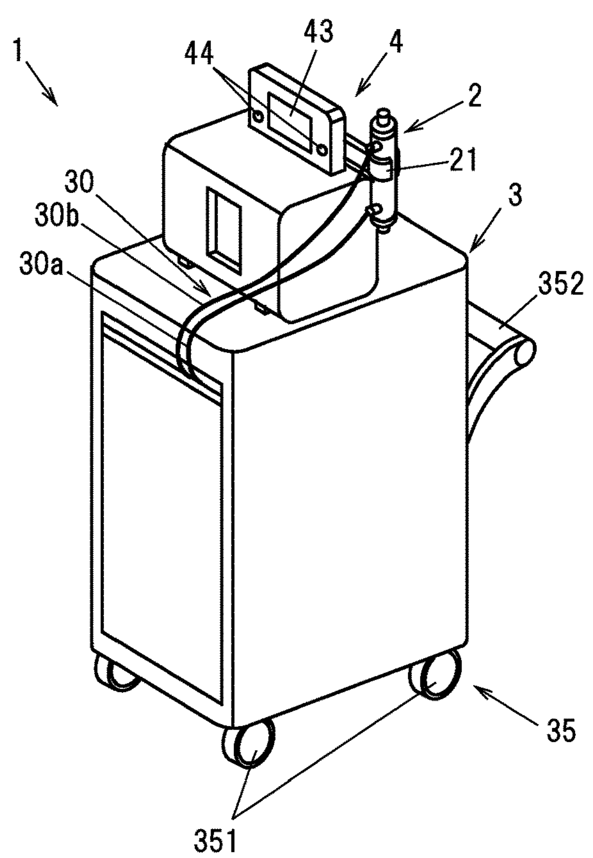
FIG. 1A is a diagram illustrating the appearance of a blood purification device in an embodiment of the present invention and is a perspective view when an extracorporeal circulation unit is attached to a dialysate supply-and-discharge unit.
Figure 1B:
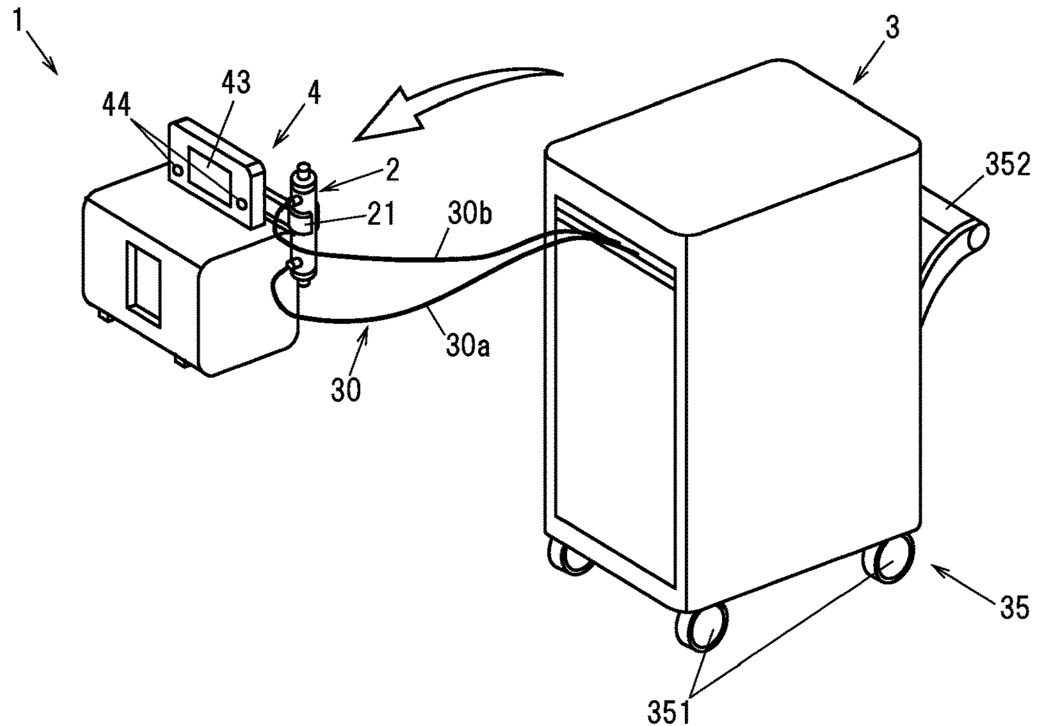
FIG. 1B is a diagram showing the appearance of the blood purification device in the embodiment of the invention and is a perspective view when the extracorporeal circulation unit is detached from the dialysate supply-and-discharge unit.
Figure 2:
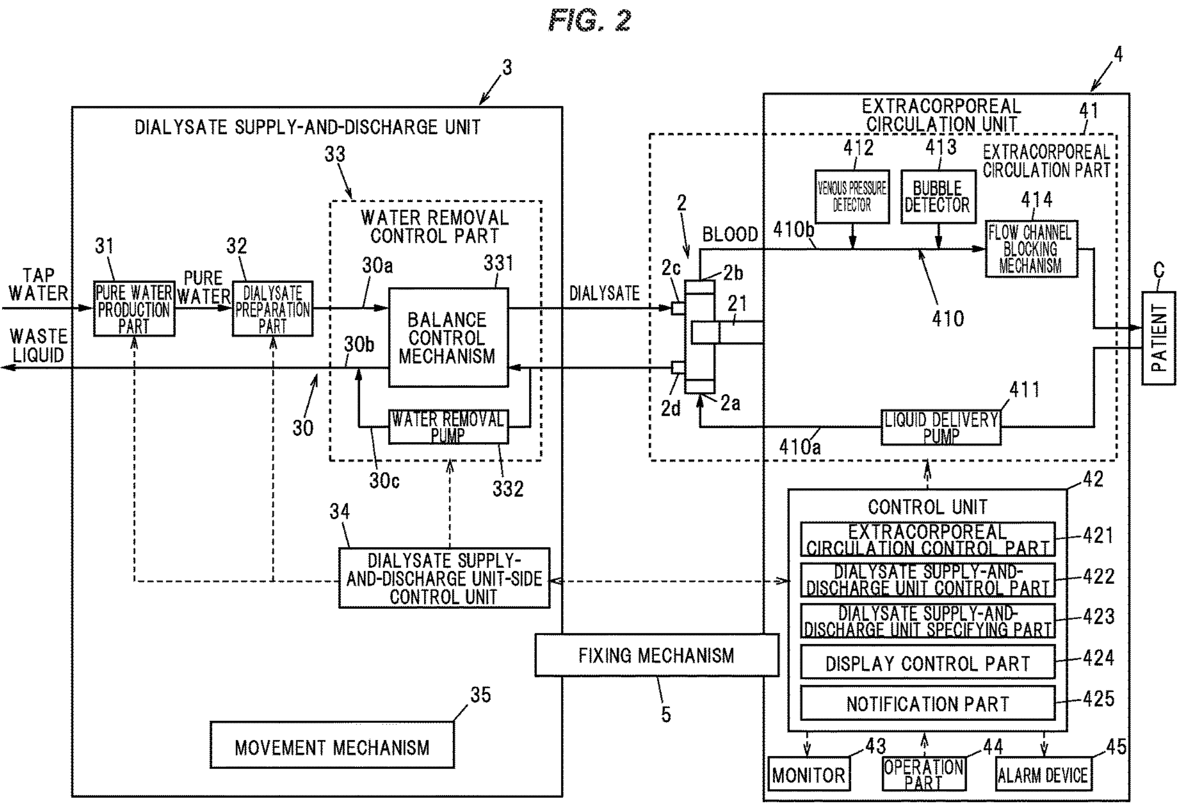
FIG. 2 is a schematic configuration diagram illustrating the blood purification device in the embodiment of the invention.

FIGS. 1A and 1B are diagrams illustrating the appearance of a blood purification device in the present embodiment, wherein FIG. 1A is a perspective view when an extracorporeal circulation unit is attached to a dialysate supply-and-discharge unit and FIG. 1B is a perspective view when the extracorporeal circulation unit is detached from the dialysate supply-and-discharge unit. FIG. 2 is a schematic configuration diagram illustrating the blood purification device in the present embodiment.

As shown in FIGS. 1A, 1B and 2, a blood purification device 1 is a device to perform blood purification treatment through a blood purifier 2 and includes a dialysate supply-and-discharge unit 3 that supplies a dialysate to the blood purifier 2 and discharges a waste liquid from the blood purifier 2, and an extracorporeal circulation unit 4 including an extracorporeal circulation part 41 to extracorporeally circulate blood of a patient through the blood purifier 2.

Blood Purifier 2

The blood purifier 2 is also called a dialyzer and includes a blood purification membrane (hollow fiber hemodialysis membrane, or hemodiafiltration membrane, flat hemodialysis membrane, or hemofiltration membrane) thereinside. The blood purifier 2 has a blood inlet 2*a* to introduce blood and a blood outlet 2*b* to discharge the introduced blood, as well as a dialysate inlet 2*c* to introduce dialysate and a dialysate outlet 2*d* to discharge the introduced dialysate. In the dialysis device 2, blood is purified by bringing the blood into contact with the dialysate through the blood purification membrane. In the present embodiment, the blood purifier 2 is detachably attached to the extracorporeal circulation unit 4 through a blood purifier fixing jig 21. In this regard, however, the position to attach the blood purifier 2 is not limited thereto, and the blood purifier 2 may be attached to the dialysate supply-and-discharge unit 3 or a dedicated stand, etc.

Dialysate Supply-and-Discharge Unit 3

The dialysate supply-and-discharge unit 3 has a pure water production part 31, a dialysate preparation part 32, a water removal control part 33, and a dialysate supply-and-discharge unit-side control unit 34. The dialysate supply-and-discharge unit 3 also has a dialysate supply-and-discharge unit-side tube 30 to convey the dialysate and the waste liquid. The dialysate supply-and-discharge unit-side tube 30 is composed of a supply-side tube 30*a* to supply the dialysate to the blood purifier 2 and a discharge-side tube 30*b* to discharge the waste liquid from the blood purifier 2.

The pure water production part 31 is provided on the supply-side tube 30*a* and is configured, e.g., to produce pure water (RO water) by using a reverse osmosis membrane (RO membrane) and removing impurities from tap water supplied externally through the supply-side tube 30*a*. In this regard, the pure water production part 31 can be omitted, and the configuration may be such that pure water is externally supplied to the dialysate supply-and-discharge unit 3.

The dialysate preparation part 32 is provided on the supply-side tube 30*a* and is configured to prepare dialysate from pure water supplied from the pure water production part 31 through the supply-side tube 30*a* and a dialysate concentrate made of a concentrated solution or powder. In this regard, the dialysate preparation part 32 can also be omitted, and the configuration may be such that, e.g., dialysate is supplied to the dialysate supply-and-discharge unit 3 from an external dialysate supply device or bag, etc.

The water removal control part 33 controls the amount of water removed from blood, and has a balance control mechanism 331 that delivers liquids so that the amount of the dialysate supplied to the blood purifier 2 is equal to the amount of waste liquid, and a water removal pump 332. The balance control mechanism 331 is placed over the supply-side tube 30*a* from the dialysate preparation part 32 to the blood purifier 2 and the discharge-side tube 30*b* extending from the blood purifier 2 and drawn into the dialysate supply-and-discharge unit 3. The balance control mechanism 331 is constructed from, e.g., a dual pump which maintains equality of the supplied liquid and the waste liquid by reciprocating movement of a plunger between two pump chambers with the same volume, etc.

A bypass tube 30*c* which bypasses the balance control mechanism 331 is provided on the discharge-side tube 30*b*, and the water removal pump 332 is arranged on the bypass tube 30*c*. By driving the water removal pump 332, the amount of the waste liquid is increased to more than the amount of the dialysate supplied to the blood purifier 2 and water is removed from the blood. The amount of water removed from the blood can be controlled by controlling drive of the water removal pump 332. In this regard, the specific structure of the water removal control part 33 is not limited to that shown in the drawing, and the configuration may be such that, e.g., the bypass tube 30*c* and the water removal pump 332 are omitted, liquid delivery pumps are respectively placed on the supply-side tube 30*a* and the discharge-side tube 30*b* instead of providing the balance control mechanism 331, the flow rates of the dialysate and the waste liquid are controlled separately by the two liquid delivery pumps, and the removed water amount is controlled based on a difference in the flow rate between the dialysate and the waste liquid.

The supply-side tube 30*a* and the discharge-side tube 30*b* located on the blood purifier 2 side relative to the water removal control part 33 are drawn to the outside of the dialysate supply-and-discharge unit 3, and ends of the drawn-out supply-side tube 30*a* and discharge-side tube 30*b* are connected to the blood purifier 2. In more particular, an end (downstream end) of the supply-side tube 30*a* is connected to the dialysate inlet 2*c* of the blood purifier 2, and an end (upstream end) of the discharge-side tube 30*b* is connected to the dialysate outlet 2*d* of the blood purifier 2. The discharge-side tube 30*b* extending from the water removal control part 33 toward the side opposite to the blood purifier 2 (toward the downstream side in the waste liquid flow) is drawn out to the outside of the dialysate supply-and-discharge unit 3, and the waste liquid is discharged to the outside of the dialysate supply-and-discharge unit 3. However, the configuration is not limited thereto, and a waste liquid tank to store the waste liquid may be provided in the dialysate supply-and-discharge unit 3.

As described above, in the present embodiment, tubes to convey the dialysate and the waste liquid (in this example, the supply-side tube 30*a* and the discharge-side tube 30*b*) are configured to directly connect the dialysate supply-and-discharge unit 3 to the blood purifier 2 without interposition of the extracorporeal circulation unit 4. In other words, tubes to convey the dialysate and the waste liquid are not provided in the extracorporeal circulation unit 4. This eliminates the need for a liquid tube connecting the dialysate supply-and-discharge unit 3 to the extracorporeal circulation unit 4, ease of handling is improved and the cost is reduced by simplifying the structure. The tube to convey the dialysate or the waste liquid (the dialysate supply-and-discharge unit-side tube 30) is desirably a fixed tube and is cleaned, disinfected and used repeatedly since the running cost is very high if disposable. The tubes to convey the dialysate and the waste liquid (in this example, the supply-side tube 30*a* and the discharge-side tube 30*b*) may be partially arranged in the extracorporeal circulation unit 4. This allows exposed portions of the tubes extending from the blood purifier 2 to be shortened, and ease of handling is improved.

The dialysate supply-and-discharge unit-side control unit 34 communicates with a control unit 42 (described later) and controls the pure water production part 31, the dialysate preparation part 32 and the water removal control part 33 in accordance with instructions from the control unit 42. The dialysate supply-and-discharge unit-side control unit 34 is realized by appropriately combining an arithmetic element such as CPU, a memory, software, interface and a communication unit, etc. The configuration may be such that the dialysate supply-and-discharge unit-side control unit 34 is omitted and the control unit 42 directly controls the pure water production part 31, the dialysate preparation part 32 and the water removal control part 33. When the pure water production part 31 or the dialysate preparation part 32 is configured as a separate component, the dialysate supply-and-discharge unit-side control unit 34 or the control unit 42 can be configured to cooperate with a control unit mounted on the pure water production part 31 or the dialysate preparation part 32 configured as a separate component and operate in conjunction therewith during blood purification treatment. Furthermore, the dialysate supply-and-discharge unit-side control unit 34 is desirably configured to be able to operate the dialysate supply-and-discharge unit 3 even when a display is not provided or even when the dialysate supply-and-discharge unit 3 is alone (in a state of being detached from the extracorporeal circulation unit 4). This makes it possible to clean and disinfect the dialysate supply-and-discharge unit 3 alone.

Although it is not shown in the drawing, the dialysate supply-and-discharge unit 3 may further include, e.g., a mechanism to adjust temperature of the dialysate, a deaeration mechanism to remove dissolved oxygen in the dialysate, a filter to remove fine particulates (endotoxin, etc.) in the dialysate, a blood leak detector to detect blood leakage, or a mechanism to measure solute concentrations in the dialysate after passing through the blood purifier 2 by irradiation with ultraviolet rays and determine dialysis efficiency. In addition, the dialysate supply-and-discharge unit 3 may further include a dialysate regeneration part to regenerate used dialysate. The dialysate regeneration part is configured to include, e.g., an adsorber that adsorbs and removes ammonia, and an injection part to inject an infusion solution to adjust the components of the dialysate.

The dialysate supply-and-discharge unit 3 is heavier than the extracorporeal circulation unit 4 (described later). Therefore, to easily move the dialysate supply-and-discharge unit 3 and increase convenience and ease of handling, the dialysate supply-and-discharge unit 3 desirably includes a movement mechanism 35 to move the dialysate supply-and-discharge unit 3 on a floor. Providing the movement mechanism 35 also makes it easier to perform swap-out maintenance (described later), which further improves maintainability. In the present embodiment, casters 351 are provided on the bottom of the dialysate supply-and-discharge unit 3, and a handle 352 to hold when moving the dialysate supply-and-discharge unit 3 is provided on a side portion of the dialysate supply-and-discharge unit 3 (see FIGS. 1A and 1B). However, the specific structure of the movement mechanism 35 is not limited thereto.

Although it is not shown in the drawing, power is externally supplied to the dialysate supply-and-discharge unit 3. In this regard, the dialysate supply-and-discharge unit 3 may be configured to include a backup power supply such as battery so that power is supplied from the backup power supply when the external power supply is interrupted during blood purification treatment. Furthermore, it may be configured to supply power from the dialysate supply-and-discharge unit 3 to the extracorporeal circulation unit 4. The form of power supply to the extracorporeal circulation unit 4 will be described later.

Extracorporeal Circulation Unit 4

The extracorporeal circulation unit 4 has the extracorporeal circulation part 41 having a blood tube (blood circuit) 410 capable of extracorporeally circulating blood of a patient C, and the control unit 42.

The blood tube 410 is formed of, e.g., a flexible tube, etc. The blood tube 410 is composed of an artery-side blood tube 410*a* through which the blood taken from a blood vessel of the patient C is guided to the blood inlet 2*a* of the blood purifier 2, and a vein-side blood tube 410*b* through which the blood discharged from the blood outlet 2*b* of the blood purifier 2 returns to the patient C. In the present embodiment, the blood tube 410 is detachably provided in the extracorporeal circulation unit 4. This allows the blood tube 410 to be disposable, i.e., single-use, which enhances maintainability. The blood tube 410 is not shown in FIGS. 1A and 1B.

The extracorporeal circulation part 41 has a liquid delivery pump 411 that is placed on the artery-side blood tube 410*a* and circulates the blood. The liquid delivery pump 411 is constructed from, e.g., a peristaltic pump which forces the blood to flow toward the blood purifier 2 by squeezing a tube. The extracorporeal circulation part 41 also has a venous pressure detector 412 which is placed on the vein-side blood tube 410*b* to measure pressure of the blood flowing through the blood tube 410, and a bubble detector 413 which detects air bubbles in the blood. The bubble detector 413 is configured to have, e.g., a pair of ultrasonic vibration elements (a means for generating oscillation and a means for receiving oscillation) formed of piezoelectric elements. A flow channel blocking mechanism 414 is also placed on the vein-side blood tube 410*b* and closes the vein-side blood tube 410*b* to stop the extracorporeal circulation of the blood when an abnormality occurs, such as when air bubbles are detected by the bubble detector 413.

In the blood purification device 1 of the present embodiment, the extracorporeal circulation unit 4 is configured as a separate component from the dialysate supply-and-discharge unit 3, and the control unit 42 capable of controlling the dialysate supply-and-discharge unit 3 and the extracorporeal circulation unit 4 is mounted on the extracorporeal circulation unit 4. The control unit 42 is realized by appropriately combining an arithmetic element such as CPU, a memory, software, interface and a communication unit, etc. The details of the control unit 42 will be described later. Although the control unit 42 is mounted on the extracorporeal circulation unit 4 in the present embodiment, the control unit 42 can be mounted on the dialysate supply-and-discharge unit 3. That is, the dialysate supply-and-discharge unit 3 and the extracorporeal circulation unit 4 may be configured to be controllable by a control unit mounted on the dialysate supply-and-discharge unit 3. This allows the dialysate supply-and-discharge unit 3 to be used alone.

The extracorporeal circulation unit 4 is configured to be detachable from the dialysate supply-and-discharge unit 3 (see FIGS. 1A and 1B). This allows use in various layouts according to the situation, e.g., a layout in which only the extracorporeal circulation unit 4 is placed close to the patient C and the dialysate supply-and-discharge unit 3 is placed at a distant position. Although the example in which the extracorporeal circulation unit 4 is attached on the top of the dialysate supply-and-discharge unit 3 is shown in FIGS. 1A and 1B, it is not limited thereto. For example, the two units 3 and 4 may be arranged side by side on the left and right or arranged front and back.

The blood purification device 1 also includes a fixing mechanism 5 that fixes the extracorporeal circulation unit 4 and the dialysate supply-and-discharge unit 3 to each other when the extracorporeal circulation unit 4 is attached to the dialysate supply-and-discharge unit 3. This suppresses falling of the extracorporeal circulation unit 4 from the dialysate supply-and-discharge unit 3 when moving the blood purification device 1 or even when a person, etc. unintentionally bumps into the blood purification device 1. The specific structure of the fixing mechanism 5 is not limited, and it is possible to use, e.g., a one-touch fixing mechanism 5 that uses a latch mechanism, etc. The fixing mechanism 5 is not shown in FIGS. 1A and 1B.

The extracorporeal circulation unit 4 also has a monitor 43 to display progress of dialysis and operation parts 44 to perform an operation related to blood purification treatment. The monitor 43 is provided so as to protrude from the top of the extracorporeal circulation unit 4 in the present embodiment as shown in FIGS. 1A and 1B, but the position or installation layout of the monitor 43 is not limited thereto. For example, the monitor 43 which is large in size may be provided so as to cover the front of the extracorporeal circulation unit 4. In addition, although the operation parts 44 are provided on both sides of the monitor 43 in the present embodiment, the positions or layout of the operation parts 44 are not limited thereto. In addition, the monitor 43 may be configured as a touch panel so that the monitor 43 also serves as the operation part 44. By providing the monitor 43 and the operation parts 44 on the extracorporeal circulation unit 4 which is relatively lightweight and placed close to the patient C, the patient C can easily check the progress of treatment or can operate the unit and convenience can be improved.

The monitor 43 and the operation part 44 may be configured as separate components from the extracorporeal circulation unit 4 and can be configured to communicate with the control unit 42 of the extracorporeal circulation unit 4 for display and operation. In this case, the monitor 43 and the operation part 44 can be composed of, e.g., a dedicated operation terminal, or a smartphone or tablet, etc. That is, at least one of the monitor 43 or the operating part 44 may be provided separately from the dialysate supply-and-discharge unit 3 and the extracorporeal circulation unit 4, and configured to be able to wirelessly communicate with the dialysate supply-and-discharge unit 3 and the extracorporeal circulation unit 4. In this regard, the monitor 43 and the operating part 44 may be configured to perform wired communication with the dialysate supply-and-discharge unit 3 or the extracorporeal circulation unit 4. Furthermore, the monitor 43 and the operating part 44 may be mounted on the dialysate supply-and-discharge unit 3.

The control unit 42 has an extracorporeal circulation control part 421, a dialysate supply-and-discharge unit control part 422, a dialysate supply-and-discharge unit specifying part 423, a display control part 424 and a notification part 425. The extracorporeal circulation control part 421 controls the extracorporeal circulation part 41. The dialysate supply-and-discharge unit control part 422 communicates with the dialysate supply-and-discharge unit-side control unit 34 and controls the dialysate supply-and-discharge unit 3 through the dialysate supply-and-discharge unit-side control unit 34. In this regard, the communication between the control unit 42 and the dialysate supply-and-discharge unit-side control unit 34 may be wired communication or may be wireless communication. When the communication between the control unit 42 and the dialysate supply-and-discharge unit-side control unit 34 is wired communication, the two units 3 and 4 are connected by a cable. This cable may be used for both communication and power supply purposes.

The dialysate supply-and-discharge unit specifying part 423 specifies the model, serial number, software version, etc. (hereinafter referred to as "unit information") of the dialysate supply-and-discharge unit 3 used. The dialysate supply-and-discharge unit specifying part 423 specifies the unit information by, e.g., communicating (wired communication or wireless communication) with the dialysate supply-and-discharge unit-side control unit 34. However, it is not limited thereto, and the dialysate supply-and-discharge unit specifying part 423 may be configured to specify the unit information of the dialysate supply-and-discharge unit 3 used based on, e.g., information input through the operation part 44, and the specific method for specifying the dialysate supply-and-discharge unit 3 used is not particularly limited.

It is more desirable that the control unit 42 have a consumable component identification unit (not shown) that not only specifies the dialysate supply-and-discharge unit 3 but also can specify the extracorporeal circulation part 41 (the blood tube 410) and the blood purifier 2. For example, the control unit 42 may be configured to include, e.g., a code reader that reads a two-dimensional code such as a QR code (registered trademark) or an identification code such as bar code attached to the extracorporeal circulation part 41 (the blood tube 410) or the blood purifier 2, and specify the extracorporeal circulation part 41 (the blood tube 410) or the blood purifier 2 based on the reading result of the code reader. Furthermore, the control unit 42 may be configured to use wireless tag technology such as RFID to specify the extracorporeal circulation part 41 (the blood tube 410) or the blood purifier 2.

The display control part 424 controls display on the monitor 43. The display control part 424 may be configured to switch items or selection options, etc. to be displayed on the monitor 43 according to the unit information (e.g., the model, etc.) specified by the dialysate supply-and-discharge unit specifying part 423.

When an abnormality in the extracorporeal circulation unit 4 or the dialysate supply-and-discharge unit 3 is detected, the notification part 425 notifies the detection of the abnormality. An abnormality in the extracorporeal circulation unit 4 is detected by, e.g., the venous pressure detector 412 or the bubble detector 413. An abnormality in the dialysate supply-and-discharge unit 3 is notified, e.g., to the control unit 42 through the dialysate supply-and-discharge unit-side control unit 34. The notification part 425 may be configured to be able to change the notification destination according to the unit information of the dialysate supply-and-discharge unit 3 specified by the dialysate supply-and-discharge unit specifying part 423. The extracorporeal circulation unit 4 may have an alarm device 45 such as light-emitting device or buzzer, and the notification part 425 may be configured to notify detection of an abnormality by driving the alarm device 45 of the extracorporeal circulation unit 4. In addition, when, e.g., at-home use is expected, the notification part 425 may be configured to provide notification by an e-mail, etc., to a facility or caregiver who supports treatment of the patient C, in addition to notification by the alarm device 45.

The extracorporeal circulation unit 4 may be powered from outside the unit, or may include a battery thereinside, or may use a combination of power supply from the outside and a battery. Alternatively, the configuration may be such that power is supplied from the dialysate supply-and-discharge unit 3 to the extracorporeal circulation unit 4. For example, the configuration may be such that the dialysate supply-and-discharge unit 3 and the extracorporeal circulation unit 4 are connected by a cable at all times and power is supplied from the dialysate supply-and-discharge unit 3 to the extracorporeal circulation unit 4 by the cable. In addition, the configuration can be such that the cable as described above is omitted and the battery inside the extracorporeal circulation unit 4 is charged with power supplied from the dialysate supply-and-discharge unit 3 to the extracorporeal circulation unit 4 when the extracorporeal circulation unit 4 is attached to the dialysate supply-and-discharge unit 3. In this case, power supply from the dialysate supply-and-discharge unit 3 to the extracorporeal circulation unit 4 may be either a contact type or a non-contact type.

Functions and Effects of the Embodiment

As described above, the blood purification device 1 in the present embodiment includes the dialysate supply-and-discharge unit 3 that supplies a dialysate to the blood purifier 2 and discharges a waste liquid from the blood purifier 2, the extracorporeal circulation unit 4 including the extracorporeal circulation part 41 to extracorporeally circulate blood of a patient through the blood purifier 2, and the control unit 42 capable of controlling the dialysate supply-and-discharge unit 3 and the extracorporeal circulation unit 4. The dialysate supply-and-discharge unit 3 includes the water removal control part 33 to control an amount of water removed from the blood, and the extracorporeal circulation unit 4 is configured as a separate component from the dialysate supply-and-discharge unit 3.

From the viewpoint of reducing running costs, the tubes for dialysate and waste liquid (the dialysate supply-and-discharge unit-side tube 30) are desirably fixed tubes as mentioned above. In this case, the tubes for dialysate and waste liquid are cleaned, disinfected and used repeatedly, hence, it is desirable to perform maintenance relatively frequently. In the present embodiment, since the extracorporeal circulation unit 4 is configured as a separate component from the dialysate supply-and-discharge unit 3, only the dialysate supply-and-discharge unit 3 can be replaced with a maintained dialysate supply-and-discharge unit 3 by delivery, etc., i.e., it is possible to perform swap-out maintenance, which greatly improves maintainability. Regarding the extracorporeal circulation unit 4, maintenance frequency can be minimized since the blood tube 410 is disposable, i.e., single-use.

If, e.g., the water removal control part 33 is mounted on the extracorporeal circulation unit 4 in the similar manner as the Patent Literature 2, portions of the tubes for dialysate and waste liquid are positioned in the extracorporeal circulation unit 4, hence, the portions of these tube needs to be disposable, i.e., single-use, to enhance maintainability and this causes an increase in the running costs. On the other hand, if portions of these tubes are composed of fixed tubes, it is necessary to frequently perform maintenance on the extracorporeal circulation unit 4, and maintainability is reduced.

Configuring the extracorporeal circulation unit 4 and the dialysate supply-and-discharge unit 3 as separate components also allows, e.g., only the extracorporeal circulation unit 4 to be placed close to the patient C, which increases the degree of freedom in arrangement and improves convenience or ease of handling.

Furthermore, in the blood purification device 1 of the present embodiment, the control unit 42 is mounted on the extracorporeal circulation unit 4. Therefore, even if some kind of malfunction occurs in the dialysate supply-and-discharge unit 3, the dialysate supply-and-discharge unit 3 can be detached and replaced with a maintained unit 3 while continuously performing extracorporeal circulation. When some kind of malfunction occurs on the dialysate supply side in conventional integrated-type blood purification devices, it is necessary to return all the blood to the patient, stop the blood purification treatment, and start new blood purification treatment with another device, which is very time-consuming and labor-intensive and also burdensome for the patient. According to the present embodiment, it is possible to save such time and labor and reduce a burden on the patient.

Furthermore, in case of the blood purification device 1 in the present embodiment, the extracorporeal circulation unit 4 detached from the dialysate supply-and-discharge unit 3 can be used alone for treatment other than hemodialysis (can be used for, e.g., hemoadsorption therapy). The detached dialysate supply-and-discharge unit 3 alone can be separately cleaned and disinfected.

Other Embodiments

Figure 3:
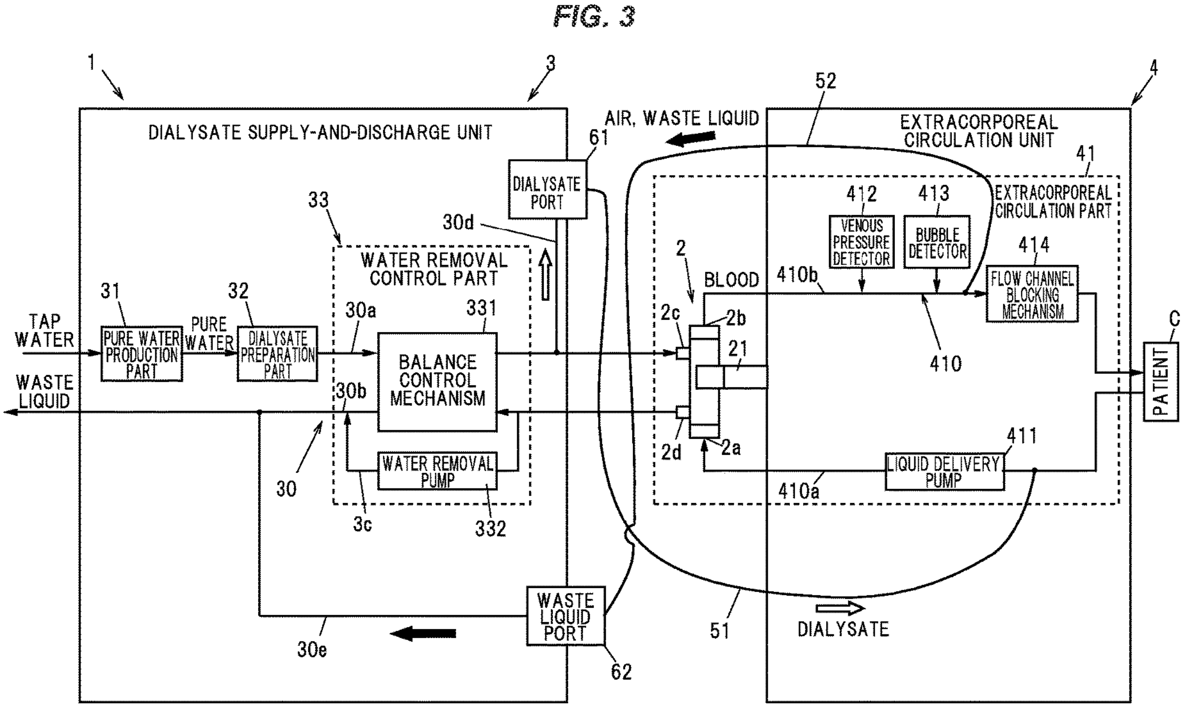
FIG. 3 is a schematic configuration diagram illustrating the blood purification device in an embodiment of the invention.

Although it is not mentioned in the above embodiment, a replacement fluid line 51 to guide the dialysate into the blood tube 410 and an overflow line 52 to discharge air or waste liquid from the blood tube 410 may be further included as shown in FIG. 3. One end of the replacement fluid line 51 is connected to the artery-side blood tube 410*a* of the blood tube 410 (the artery-side blood tube 410*a* on the patient C side relative to the liquid delivery pump 411). The other end of the replacement fluid line 51 is connected to a dialysate port 61 provided on the dialysate supply-and-discharge unit 3. One end of the overflow line 52 is connected to the vein-side blood tube 410*b* of the blood tube 410 (the vein-side blood tube 410*b* between the bubble detector 413 and the flow channel blocking mechanism 414). The one end of the overflow line 52 may alternatively be connected to a gas-liquid separator provided on the vein-side blood tube 410*b*. The other end of the overflow line 52 is connected to a waste liquid port 62 provided on the dialysate supply-and-discharge unit 3. A dialysate port tube 30*d* branched from the supply-side tube 30*a* on the downstream side of the balance control mechanism 331 is connected to the dialysate port 61 and the dialysate is supplied to the dialysate port 61 through the dialysate port tube 30*d*. The waste liquid port 62 is connected to the discharge-side tube 30*b* on the downstream side of the balance control mechanism 331 through a waste liquid port tube 30*c*.

The replacement fluid line 51 and the overflow line 52 are used, e.g., at the time of fluid replacement to supply the dialysate into the blood tube 410 during blood purification treatment, at the time of priming to fill the blood tube 410 with the dialysate before blood purification treatment, or at the time of reinfusion of blood where the dialysate is introduced into the blood tube 410 to return blood to the patient C after blood purification treatment. For example, at the time of priming, the dialysate is supplied from the supply-side tube 30*a* into the blood tube 410 through the dialysate port tube 30*d*, the dialysate port 61 and the replacement fluid line 51 (open arrows in the drawing) by driving the liquid delivery pump 411 provided on the blood tube 410. As the dialysate is supplied, the air in the blood tube 410 is discharged to the discharge-side tube 30*b* through the overflow line 52, the waste liquid port 62 and the waste liquid port tube 30*e* (filled arrows in the drawing) and the blood tube 410 is filled with the dialysate.

Although the example in which the dialysate port 61 and the waste liquid port 62 are provided on the dialysate supply-and-discharge unit 3 is shown in FIG. 3, the configuration is not limited thereto and the dialysate port 61 and the waste liquid port 62 may be provided on the extracorporeal circulation unit 4. In this case, the dialysate port tube 30*d* and the waste liquid port tube 30*e* extend from the dialysate supply-and-discharge unit 3 to the extracorporeal circulation unit 4, and portions of the dialysate port tube 30*d* and the waste liquid port tube 30*e* are formed in the extracorporeal circulation unit 4. Providing the dialysate port 61 and the waste liquid port 62 on the extracorporeal circulation unit 4 makes it easier to connect the replacement fluid line 51 and the overflow line 52 to the dialysate port 61 and the waste liquid port 62 and also allows the replacement fluid line 51 and the overflow line 52 to be reduced in length. The replacement fluid line 51 and the overflow line 52 are preferably disposable, i.e., single-use, in the same manner as the blood tube 410.

Summary of the Embodiment

Technical ideas understood from the embodiment will be described below citing the reference signs, etc., used for the embodiment. However, each reference sign, etc., described below is not intended to limit the constituent elements in the claims to the members, etc., specifically described in the embodiment.

[1] A blood purification device (1) to perform blood purification treatment through a blood purifier (2), the blood purification device (1) comprising: a dialysate supply-and-discharge unit (3) that supplies a dialysate to the blood purifier (2) and discharges a waste liquid from the blood purifier (2); an extracorporeal circulation unit (4) comprising an extracorporeal circulation part (41) to extracorporeally circulate blood of a patient through the blood purifier (2); and a control unit (42) capable of controlling the dialysate supply-and-discharge unit (3) and the extracorporeal circulation unit (4), wherein the dialysate supply-and-discharge unit (3) comprises a water removal control part (33) to control an amount of water removed from the blood, and wherein the extracorporeal circulation unit (4) is configured as a separate component from the dialysate supply-and-discharge unit (3).

This makes it possible to perform swap-out maintenance and it is thereby possible to realize the blood purification device (1) with improved maintainability. In addition, the degree of freedom in arrangement can be improved by providing the extracorporeal circulation unit (4) and the dialysate supply-and-discharge unit (3) as separate components.

[2] The blood purification device (1) as defined by [1], wherein the control unit (42) is mounted on the extracorporeal circulation unit (4).

This allows the extracorporeal circulation unit (4) to be used alone, and convenience is thereby further improved.

[3] The blood purification device (1) as defined by [2], wherein the control unit (42) comprises a dialysate supply-and-discharge unit specifying part (423) to specify the dialysate supply-and-discharge unit (3) used.

It is thereby possible to make the dialysate supply-and-discharge unit (3) operate correctly according to the software version or model number (hardware version) of the specified dialysate supply-and-discharge unit (3) (erroneous operations due to version differences, etc. can be suppressed). In addition, it is also possible to provide, e.g., a display screen or operation screen corresponding to the dialysate supply-and-discharge unit (3) used, and convenience is thereby improved.

[4] The blood purification device (1) as defined by [1], wherein the control unit (42) is mounted on the dialysate supply-and-discharge unit (3).

This allows the dialysate supply-and-discharge unit (3) to be used alone, and convenience is thereby further improved.

[5] The blood purification device (1) as defined by any one of [1] to [4], wherein a tube (30) to convey the dialysate and the waste liquid is configured to directly connect the dialysate supply-and-discharge unit (3) to the blood purifier (2) without interposition of the extracorporeal circulation unit (4).

Since the tubes to convey the dialysate and the waste liquid are not provided on the extracorporeal circulation unit (4), it is necessary to regularly perform maintenance on only the dialysate supply-and-discharge unit (3) even when the tubes to convey the dialysate and the waste liquid are fixed tubes, hence, it is possible to achieve both running cost reduction and improvement in maintainability.

[6] The blood purification device (1) defined as any one of [1] to [5], wherein the extracorporeal circulation unit (4) is configured to be detachable from the dialysate supply-and-discharge unit (3), and wherein a fixing mechanism (5) is provided to fix the extracorporeal circulation unit (4) and the dialysate supply-and-discharge unit (3) to each other when the extracorporeal circulation unit (4) is attached to the dialysate supply-and-discharge unit (3).

It is thereby possible to further improve the degree of freedom in arrangement, suppress falling of the extracorporeal circulation unit (4) from the dialysate supply-and-discharge unit (3), and increase safety.

[7] The blood purification device (1) as defined by any one of [1] to [6], wherein a blood tube (410) to convey blood is detachably provided in the extracorporeal circulation unit (4).

This allows the blood tube (410) to be disposable. i.e., single-use, and maintainability is thereby further improved.

[8] The blood purification device (1) as defined by any one of [1] to [7], wherein the extracorporeal circulation unit (4) comprises a monitor (43) to display progress of dialysis and an operation part (44) to perform an operation related to the blood purification treatment.

Since the monitor (43) and the operation part (44) are provided on the extracorporeal circulation unit (4) which is used close to the patient C, the patient C can easily know progress of treatment and operate the device during the blood purification treatment, and convenience is thereby improved.

[9] The blood purification device (1) as defined by any one of [1] to [7], wherein at least one of a monitor (43) to display progress of dialysis or an operation part (44) to perform an operation related to the blood purification treatment is provided separately from the dialysate supply-and-discharge unit (3) and the extracorporeal circulation unit (4) and is configured to be able to wirelessly communicate with the dialysate supply-and-discharge unit (3) or the extracorporeal circulation unit (4).

As a result, e.g., the monitor (43) and the operation part (44) can be realized by a portable terminal, etc., which allows the patient C to easily monitor the progress of treatment or operate the device during the blood purification treatment and also allows medical workers and caregivers to easily remotely monitor the progress of treatment or operate the device, hence, convenience is improved.

[10] The blood purification device (1) as defined by any one of [1] to [9], wherein the dialysate supply-and-discharge unit (3) comprises a movement mechanism (35) to move the dialysate supply-and-discharge unit (3) on a floor.

This makes it easier to move the relatively heavy dialysate supply-and-discharge unit (3), which improves convenience and ease of handling and makes it easier to perform swap-out maintenance.

[11] The blood purification device (1) as defined by any one of [1] to [10], wherein the dialysate supply-and-discharge unit (3) comprises a dialysate preparation part (32) to prepare the dialysate from pure water supplied thereto and a dialysate concentrate.

This eliminates the need for separately preparing a device to produce dialysate and it is possible to realize a personal blood purification device (1) suitable for treatment in a private room in a medical institution or at home, etc.

[12] The blood purification device (1) as defined by [11], wherein the dialysate supply-and-discharge unit (3) comprises a pure water production part (31) to produce pure water from externally supplied tap water, and wherein the dialysate preparation part (32) prepares the dialysate from pure water supplied from the pure water production part (31) and a dialysate concentrate.

This eliminates the need for separately preparing a device to produce pure water and it is possible to realize a personal blood purification device (1) more suitable for treatment at home, etc.

Although the embodiments of the invention have been described, the invention according to claims is not to be limited to the embodiments described above. Further, please note that not all combinations of the features described in the embodiments are necessary to solve the problem of the invention.

In addition, the invention can be appropriately modified and implemented without departing from the gist thereof.

For example, the dialysate is directly introduced into the blood tube 410 in some blood purification treatments such as on-line HDF (Hemo Dialysis Filtration), even though it is not mentioned in the above embodiment. When performing such treatment, a replacement fluid tube to guide the dialysate to the blood tube 410 may be provided from the dialysate supply-and-discharge unit 3 to the extracorporeal circulation unit 4. In addition, a priming tube to supply or discharge a priming liquid such as an online dialysate or physiological saline may be provided on the blood tube 410. In this case, however, it is desirable to configure the replacement fluid tube or the priming tube to be detachable from the blood tube 410 or to configure the replacement fluid tube or the priming tube to be disposable, i.e., single-use, to enhance maintainability.

In addition, although the control unit 42, which is capable of controlling the dialysate supply-and-discharge unit 3 and the extracorporeal circulation unit 4 so that the two units operate in conjunction with each other, is mounted on the extracorporeal circulation unit 4 in the above embodiment, it is not limited thereto. The control unit 42 may be mounted on the dialysate supply-and-discharge unit 3 or may be mounted on a separate unit from the two units 3 and 4.

REFERENCE SIGNS LIST

1 blood purification device
2 blood purifier
3 dialysate supply-and-discharge unit
30 dialysate supply-and-discharge unit-side tube
30*a* supply-side tube
30*b* discharge-side tube
30*c* bypass tube
33 water removal control part
35 movement mechanism
4 extracorporeal circulation unit
41 extracorporeal circulation part
410 blood tube
42 control unit
43 monitor
44 operation part
5 fixing mechanism

The invention claimed is:

1. A blood purification device to perform blood purification treatment through a blood purifier, the blood purification device comprising:

a dialysate supply-and-discharge unit that supplies a dialysate to the blood purifier and discharges a waste liquid from the blood purifier;

an extracorporeal circulation unit comprising an extracorporeal circulation part to extracorporeally circulate blood of a patient through the blood purifier; and a control unit capable of controlling the dialysate supply-and-discharge unit and the extracorporeal circulation unit, wherein the dialysate supply-and-discharge unit comprises a water removal control part to control an amount of water removed from the blood, the water removal control part comprising:

a balance control mechanism that delivers liquids so that an amount of the dialysate supplied to the blood purifier from the balance control mechanism is equal to an amount of the waste liquid removed from the blood purifier by the balance control mechanism, a bypass tube that bypasses the balance control mechanism, and a water removal pump for removing water from blood circulated through the extracorporeal circulation unit, the water removal pump being arranged on the bypass tube such that removal of water from the blood circulated through the extracorporeal circulation unit increases the amount of the waste liquid to be more than the amount of the dialysate supplied to the blood purifier, and wherein the extracorporeal circulation unit is configured as a separate component from the dialysate supply-and-discharge unit.

2. The blood purification device according to claim 1, wherein the control unit is mounted on the extracorporeal circulation unit.

3. The blood purification device according to claim 2, wherein the control unit comprises a dialysate supply-and-discharge unit specifying part to specify the dialysate supply-and-discharge unit used.

4. The blood purification device according to claim 1, wherein the control unit is mounted on the dialysate supply-and-discharge unit.

5. The blood purification device according to claim 1, wherein a tube to convey the dialysate and the waste liquid is configured to directly connect the dialysate supply-and-discharge unit to the blood purifier without interposition of the extracorporeal circulation unit.

6. The blood purification device according to claim 1, wherein the extracorporeal circulation unit is configured to be detachable from the dialysate supply-and-discharge unit, and wherein a fixing mechanism is provided to fix the extracorporeal circulation unit and the dialysate supply-and-discharge unit to each other when the extracorporeal circulation unit is attached to the dialysate supply-and-discharge unit.

7. The blood purification device according to claim 1, wherein a blood tube to convey blood is detachably provided in the extracorporeal circulation unit.

8. The blood purification device according to claim 1, wherein the extracorporeal circulation unit comprises a monitor to display progress of dialysis and an operation part to perform an operation related to the blood purification treatment.

9. The blood purification device according to claim 1, wherein at least one of a monitor to display progress of dialysis or an operation part to perform an operation related to the blood purification treatment is provided separately from the dialysate supply-and-discharge unit and the extracorporeal circulation unit and is configured to be able to wirelessly communicate with the dialysate supply-and-discharge unit or the extracorporeal circulation unit.

10. The blood purification device according to claim 1, wherein the dialysate supply-and-discharge unit comprises a movement mechanism to move the dialysate supply-and-discharge unit on a floor.

11. The blood purification device according to claim 1, wherein the dialysate supply-and-discharge unit comprises a dialysate preparation part to prepare the dialysate from pure water supplied thereto and a dialysate concentrate.

12. The blood purification device according to claim 11, wherein the dialysate supply-and-discharge unit comprises a pure water production part to produce pure water from externally supplied tap water, and wherein the dialysate preparation part prepares the dialysate from pure water supplied from the pure water production part and a dialysate concentrate.

* * * * *